(12) United States Patent
Zakharenko et al.

(10) Patent No.: US 9,255,268 B2
(45) Date of Patent: Feb. 9, 2016

(54) METHODS FOR DIAGNOSING AND TREATING LEARNING OR MENTAL DISORDERS

(71) Applicant: St. Jude Children's Research Hospital, Memphis, TN (US)

(72) Inventors: Stanislav S. Zakharenko, Collierville, TN (US); Laurie R. Earls, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/371,256

(22) PCT Filed: Feb. 1, 2013

(86) PCT No.: PCT/US2013/024257
§ 371 (c)(1),
(2) Date: Jul. 9, 2014

(87) PCT Pub. No.: WO2013/116589
PCT Pub. Date: Aug. 8, 2013

(65) Prior Publication Data
US 2015/0005365 A1 Jan. 1, 2015

Related U.S. Application Data

(60) Provisional application No. 61/593,947, filed on Feb. 2, 2012.

(51) Int. Cl.
| | |
|---|---|
| *C12Q 1/00* | (2006.01) |
| *C12N 15/113* | (2010.01) |
| *C12Q 1/68* | (2006.01) |
| *A61K 31/7105* | (2006.01) |

(52) U.S. Cl.
CPC .......... *C12N 15/113* (2013.01); *A61K 31/7105* (2013.01); *C12Q 1/6883* (2013.01); *C12N 2310/141* (2013.01); *C12N 2320/30* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2009/0192112 A1* | 7/2009 | Simeone et al. | 514/44 |
| 2010/0009367 A1 | 1/2010 | Sommer et al. | 435/6.16 |
| 2010/0227908 A1 | 9/2010 | Cairns | 514/44 A |

FOREIGN PATENT DOCUMENTS

WO   WO 2011/066132 A1   6/2011

OTHER PUBLICATIONS

Rogaev. (2005) Biochemistry, v.70(12):1404-7.*
Bassett et al. "Clinical Features of 78 Adults With 22q11 Deletion Syndrome" American Journal of Medical Genetics Part A 2005 138(4):307-313.
Beveridge and Cairns "MicroRNA Dysregulation in Schizophrenia" Neurobiology of Disease 2012 46:263-271.
Burn et al. "Conotruncal Anomaly Face Syndrome is Associated with a Deletion within Chomosome 22q11" Journal of Medical Genetics 1993 30:822-824.
Chow et al. "Neurocognitive Profile in 22q11 Deletion Syndrome and Schizophrenia" Schizophrenia Research 2006 87(1-3):270-278.
Earls et al. "Dysregulation of Presynaptic Calcium and Synaptic Plasticity in a Mouse Model of 22q11 Deletion Syndrome" The Journal of Neuroscience 2010 30(47):15843-15855.
Earls et al. "Age-Dependent MicroRNA Control of Synaptic Plasticity in 22q11 Deletion Syndrome and Schizophrenia" The Journal of Neuroscience 2012 32(41):14132-14144.
Gold, J. M. "Cognitive Deficits as Treatment Targets in Schizophrenia" Schizophrenia Research 2004 72:21-28.
Green, M. F. "What are the Functional Consequences of Neurocognitive Deficits in Schizophrenia?" The American Journal of Psychiatry 1996 153(3):321-330.
Green et al. "Neurocognitive Deficits and Functional Outcome in Schizophrenia: Are We Measuring the "Right Stuff"?" Schizophrenia Bulletin 2000 26(1):119-136.
Heckers et al. "Impaired Recruitment of the Hippocampus During Conscious Recollection in Schizophrenia" Nature Neuroscience 1998 1(4):318-323.
Lindsay et al. "Congenital Heart Disease in Mice Deficient for the DiGeorge Syndrome Region" Nature 1999 401:379-383.
Martin et al. "Synaptic Plasticity and Memory: An Evaluation of the Hypothesis" Annual Review of Neuroscience 2000 23:649-711.
Milner et al. "Cognitive Neuroscience and the Study of Memory" Neuron 1998 20:445-468.
Moreau et al. "Altered MicroRNA Expression Profiles in Post-Mortem Brain Samples from Individuals with Schizophrenia and Bipolar Disorder" Biological Psychiatry 2011 69(2):188-193.
Murphy et al. "High Rates of Schizophrenia in Adults with Velo-Cardio-Facial Syndrome" Archives of General Psychiatry 1999 56:940-945.
Òskarsdòttir et al. "Incidence and Prevalence of the 22q11 Deletion Syndrome: a Population-Based Study in Western Sweden" Archives of Disease in Childhood 2004 89:148-151.
Pulver et al. "Psychotic Illness in Patients Diagnosed with Velo-Cardio-Facial Syndrome and Their Relatives" 182(8):476-478 The Journal of Nervous and Mental Disorders 1994.
Ryan et al. "Spectrum of Clinical Features Associated with Interstitial Chromosome 22q11 Deletions: a European Collaborative Study" Journal of Medical Genetics 1997 34:798-804.
Scambler, P. J. and Kelly, D. "Velo-Cardio-Facial Syndrome Associated with Chromosome 22 Deletions Encompassing the DiGeorge Locus" Lancet 1992 339(8802):1138-1139.
Scambler, P. J. "The 22q11 Deletion Syndromes" Human Molecular Genetics 2000 9(16):2421-2426.
Sempere et al. "Expression Profiling of Mammalian MicroRNAs Uncovers a Subset of Brain-Expressed MicroRNAs with Possible Roles in Murine and Human Neuronal Differention" Genome Biology 2004 5:R13.
Smirnova et al. "Regulation of MiRNA Expression During Neural Cell Specification" European Journal of Neuroscience 2005 21(6):1469-1477.

(Continued)

*Primary Examiner* — Jennifer McDonald
(74) *Attorney, Agent, or Firm* — Licata & Tyrrell P.C.

(57) ABSTRACT

The present invention embraces methods for the diagnosis and treatment of learning or mental disorders such as schizophrenia using miR-25, miR-98, or miR-185.

6 Claims, No Drawings

(56) References Cited

OTHER PUBLICATIONS

Stark et al. "Altered Brain MicroRNA Biogenesis Contributes to Phenotypic Deficits in a 22q11-Deletion Mouse Model" Nature Genetics 2008 40(6):751-760.
Tamminga et al. "The Hippocampal Formation in Schizophrenia" The American Journal of Psychiatry 2010 167:1178-1193.
Weinberger et al. "Schizophrenia: New Phenes and New Genes" Biological Psychiatry 1999 46(1):3-7.
Xu et al. "Derepression of a Neuronal Inhibitor due to miRNA Dysregulation in a Schizophrenia-Related Microdeletion" Cell 2013 152:262-275.
microRNA.org Targets and Expression, Nov. 1, 2011 [online]. Retrieved from the internet: <URL: http://www.microrna.org/microrna/getMrna.do?gene=11938&utr=14414&organism=10090&matureName=mmu-miR-185#>. Especially p. 1.
International Search Report from PCT/US2013/024257, Apr. 9, 2013.
International Preliminary Report on Patentability from PCT/US2013/024257, Aug. 14, 2014.

* cited by examiner

SEQUENCE LISTING

<160> NUMBER OF SEQ ID NOS: 45

<210> SEQ ID NO 1
<211> LENGTH: 84
<212> TYPE: RNA
<213> ORGANISM: Homo sapiens

<400> SEQUENCE: 1
ggccaguguu gagaggcgga gacuugggca auugcuggac gcugcccugg gcauugcacu      60
ugucucgguc ugacagugcc ggcc                                            84

<210> SEQ ID NO 2
<211> LENGTH: 22
<212> TYPE: RNA
<213> ORGANISM: Homo sapiens

<400> SEQUENCE: 2
cauugcacuu gucucggucu ga                                              22

<210> SEQ ID NO 3
<211> LENGTH: 119
<212> TYPE: RNA
<213> ORGANISM: Homo sapiens

<400> SEQUENCE: 3
aggauucugc ucaugccagg gugagguagu aaguuguauu guugugggu agggauauua      60 ggccccaauu agaagauaac uauacaacuu acuacuuucc cuggugugug gcauauuca     119

<210> SEQ ID NO 4
<211> LENGTH: 22
<212> TYPE: RNA
<213> ORGANISM: Homo sapiens

<400> SEQUENCE: 4
ugagguagua aguuguauug uu                                              22

```
<210> SEQ ID NO 5
<211> LENGTH: 82
<212> TYPE: RNA
<213> ORGANISM: Homo sapiens

<400> SEQUENCE: 5 aggggggcgag ggauuggaga gaaaggcagu uccugauggu ccccuccccca ggggcuggcu    60 uuccucuggu ccuucccucc ca                                              82

<210> SEQ ID NO 6
<211> LENGTH: 22
<212> TYPE: RNA
<213> ORGANISM: Homo sapiens

<400> SEQUENCE: 6
uggagagaaa ggcaguuccu ga                                              22

<210> SEQ ID NO 7
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 7
gcatactccg accgttactt cagaccg                                         27

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ggtgccattg cacttgtctc                                                 20

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
tcagcatact ccgaccgtta ct                                              22

<210> SEQ ID NO 10
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 10
ggcgtaataa tcgctccatt caacaataca a                                    31

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 11
cgcaagaagt gaggtagtaa gttg                                          24

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
cggcgtaata atcgctccat tc                                            22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13
caatggagag aaaggcagtt cc                                            22

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
aatccatgag agatccctac cg                                            22

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tggagagaaa ggcagttcct                                               20

<210> SEQ ID NO 16
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 16
tggtttaccg tcccac                                                   16

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
ttcagctcct atatgatg                                                 18
```

```
<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
tagtagaccg tatagcgta                                               19

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
tatgtaacac ggtccacta                                               19

<210> SEQ ID NO 20
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 20
ctggcccgag ggacc                                                   15

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
atataataca acctgctaag                                              20

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
tggtagacta tggaacgta                                               19

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
gaacggcgtc atgcaggag                                               19

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 24
aacacaccca gctaaccttt                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
cacagctccc atctcagaac                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
tacagttgtt caaccagtta                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tacagttgtt caaccagtta                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
tgaggtagta agttgtattg                                              20

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
tgaggttggt gtactgtgtg t                                            21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
atcaacagac attaattggg c                                            21
```

```
<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
aggttacccg agcaactttg c                                              21

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
aaggttactt gttagttca                                                 19

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
cctcccacac ccaaggcttg                                                20

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
aatgacacga tcactcccgt t                                              21

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
cattgcactt gtctcggtct                                                20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
cgcttcggca gcacatatac                                                20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 37
ttcacgaatt tgcgtgtcat        20

<210> SEQ ID NO 38
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 38
gtacagctgt tgacagtgag cgactggaga gaaaggcagt tcctgatgtg aa        52

<210> SEQ ID NO 39
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 39
gccacagatg gtcaggaact ctttctctcc agctgcctac tgcctcggaa        50

<210> SEQ ID NO 40
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 40
ccatctgtgg cttcacatca ggaactgcct ttctctccag tcgctcactg tcaacagct        59

<210> SEQ ID NO 41
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 41
agctttccga ggcagtaggc agctggagag aaagagttcc tga        43

<210> SEQ ID NO 42
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 42
gtacagctgt tgacagtgag cgacaggcgg agacttgggc aattgctgtg aa        52

<210> SEQ ID NO 43
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 43
gccacagatg ggcaattgcc agtctccgcc tgctgcctac tgcctcggaa        50

```
<210> SEQ ID NO 44
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 44
ccatctgtgg cttcacagca attgcccaag tctccgcctg tcgctcactg tcaacagct      59

<210> SEQ ID NO 45
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 45
agctttccga ggcagtaggc agcaggcgga gactggcaat tgc                      43
```

METHODS FOR DIAGNOSING AND TREATING LEARNING OR MENTAL DISORDERS

This application is a U.S. National Stage Application of PCT/US2013/024257 filed Feb. 1, 2013 and claims benefit of priority to U.S. Provisional Application Ser. No. 61/593,947, filed Feb. 2, 2012, the contents of each of which are incorporated herein by reference in their entirety.

This invention was made in the course of research sponsored by the National Institute of Mental Health, grant number R01MH079079. The U.S. government has certain rights in this invention.

BACKGROUND OF THE INVENTION

Schizophrenia is a devastating disease that affects approximately 1% of the world's population and is characterized by a constellation of symptoms that includes hallucinations and delusions (positive symptoms), antisocial behavior and blunted emotions (negative symptoms), and deficits in working memory, executive function, and learning and memory (cognitive symptoms).

One well known genetic predictor of schizophrenia is the 22q11 deletion syndrome (22q11DS). This syndrome is caused by the hemizygous deletion of a 1.5 to 3 megabase region of the q arm of chromosome 22, resulting in the haploinsufficiency of 30 to 40 genes (Burn, et al. (1993) *J. Med. Genet.* 30:822; Ryan, et al. (1997) *J. Med. Genet.* 34:798; Scambler, et al. (2000) *Hum. Mol. Genet.* 9:2421; Oskarsdottir, et al. (2004) *Arch. Dis. Child* 89:148; Scambler, et al. (1992) *Lancet* 339:1138). Approximately 30% of patients with 22q11DS experience schizophrenia or schizoaffective disorder during adolescence or early adulthood (Chow, et al. (2006) *Schizophr. Res.* 87:270; Pulver, et al. (1994) *J. Nerv. Ment. Dis.* 182:476; Bassett, et al. (2005) *Am. J. Med. Genet.* 138:307). Symptoms of 22q11DS-related schizophrenia are indistinguishable from those of the idiopathic disease (Pulver, et al. (1994) supra; Chow, et al. (2006) supra; Murphy, et al. (1999) *Arch. Gen. Psychiatry* 56:940), suggesting that the biological mechanisms involved in schizophrenia arising from the 22q11.2 deletion are the same as those involved in non-deletion-related schizophrenia.

Cognitive deficits are central to schizophrenia and are among the least treatable symptoms of the disease (Gold (2004) *Schizophr. Res.* 72:21; Green (1996) *Am. J. Psychiatry* 153:321; Green, et al. (2000) *Schizophr. Bull.* 26:119). These symptoms have been linked, in part, to the hippocampus (Heckers, et al. (1998) *Nat. Neurosci.* 1:318; Tamminga, et al. (2010) *Am. J. Psychiatry* 167:1178; Weinberger (1999) *Biol. Psychiatry* 46:3), a brain region well-studied for its role in learning and memory. Mechanisms of hippocampal learning and memory have been thoroughly characterized using animal models. Synaptic plasticity at excitatory synapses has emerged as a cellular mechanism of hippocampus-related learning and memory (Martin, et al. (2000) *Annu. Rev. Neurosci.* 23:649; Milner, et al. (1998) *Neuron* 20:445) and provides an excellent means to probe cellular events related to cognition in animal models of schizophrenia.

The 22q11DS-critical region of human chromosome 22 is largely conserved on mouse chromosome 16, allowing for the generation of 22q11DS mouse models. The Df(16)1/+ mouse carries a hemizygous deletion of 23 genes in the syntenic region of mouse chromosome 16 (Lindsay, et al. (1999) *Nature* 401:379) and develops a spatial memory deficit and enhanced synaptic plasticity in the form of long-term potentiation (LTP) by 16 weeks of age (Earls, et al. (2010) *J. Neurosci.* 30:15843). This age-dependent alteration in hippocampal synaptic plasticity is caused by an aberrant increase in the protein level of the sarco(endo)plasmic reticulum ATPase (SERCA2), which maintains calcium (Ca2+) levels in the endoplasmic reticulum (ER). SERCA2 upregulation leads to increased LTP by enhancing Ca2+ entry into presynaptic cytoplasm and releasing an excess of neurotransmitter during synaptic plasticity induction. Therefore, the age-dependent synaptic abnormalities in Df(16)1/+ mice may be relevant to the cognitive decline observed at the onset of schizophrenia. Identification of the culprit genes within the 22q11DS-critical region that cause these abnormalities provides insight into the pathophysiology of schizophrenia.

A survey of miRNA expression patterns in various organ and tissue types has identified several brain-specific and brain-enriched miRNAs (Sempere, et al. (2004) *Genome Biol.* 5:R13). There are a growing number of miRNAs with well-characterized neurodevelopmental functions. miR-124 and miR-9 influence the decision of neural precursors to adopt a neuronal or glial fate. miR-124 inhibits expression of nonneuronal genes and splicing factors, and transfecting miR-124 duplexes into progenitor cells decreases the number of cells expressing glial markers (glial fibrillary acidic protein) while increasing the number of neurons (Smirnova, et al. (2005) *Eur. J. Neurosci.* 21(6):1469-77). In addition, altered expression of selected miRNAs has been shown to correlate with schizophrenia or bipolar disorder (Moreau, et al. (2011) *Biol. Psychiatry* 69:188) and miRNAs, as well as proteins regulating the biogenesis of miRNAs (e.g., DGCR8), have been suggested for use in the diagnosis and prognosis of schizophrenia (US 2010/0227908 and US 2010/0009367).

SUMMARY OF THE INVENTION

The present invention features methods for reversing age-dependent changes in neural function and treating a learning disorder or mental disorder by administering to a subject in need of treatment an effective amount of at least one microRNA (miR) selected from the group of miR-25, miR-98 and miR-185. In certain embodiments, the mental disorder is a psychiatric disease such as schizophrenia, Alzheimer's disease, bipolar disorder, schizoaffective disorder, 22q11 deletion syndrome, attention-deficit hyperactivity disorder, obsessive-compulsive disorder or autism spectrum disorder.

Additional features of this invention include methods for diagnosing the susceptibility for developing a learning or mental disorder or diagnosing whether a subject has a learning or mental disorder. These methods involve the steps of obtaining a biological sample from a subject, measuring the level of at least one microRNA (miR) selected from the group of miR-25, miR-98 and miR-185 in said sample with a microRNA specific probe, comparing the measured level to a control, and diagnosing the susceptibility or presence of a learning or mental disorder based upon a reduced level of the miRNA as compared to a control. In some embodiments, the mental disorder is a psychiatric disease such as schizophrenia, Alzheimer's disease, bipolar disorder, schizoaffective disorder, 22q11 deletion syndrome, attention-deficit hyperactivity disorder, obsessive-compulsive or autism spectrum disorder.

DETAILED DESCRIPTION OF THE INVENTION

Using a panel of mutant mice carrying hemizygous deletions of clusters of genes or individual genes within the 22q11DS-critical region, genes involved in the observed age-dependent increase in LTP were identified. This systematic screen identified Dgcr8 as a contributor to synaptic abnormalities. DGCR8 is a double-stranded RNA-binding protein that is involved in the early stages of microRNA (miR) biogenesis. The data presented herein show that the hemizygous loss of Dgcr8 causes an age-dependent increase in LTP that depends on upregulation of synaptic SERCA2. Three miRs (miR-25, -185, and -98) were found to be depleted with age in 22q11DS mouse models and are predicted to target the Serca2 transcript. Indeed, restoration of these miRs to mature hippocampus was sufficient to rescue aberrant LTP observed in Dgcr8$^{+/-}$ mice. In addition, it has now been shown that SERCA2 is also upregulated in postmortem brain samples from patients with schizophrenia. Therefore, the molecular events described in the mouse model of 22q11DS are of relevance to the mechanisms of the human disease. Accordingly, the present invention embraces methods for reversing age-dependent changes in neural function, and treating and diagnosing learning or mental disorders using miR-25, miR-185, and miR-98.

As used herein interchangeably, a "miRNA gene product," "microRNA," "miR," or "miRNA" refers to the unprocessed or processed RNA transcript from a miRNA gene. As the miRNA gene products are not translated into protein, the term "miRNA gene products" does not include proteins. The unprocessed miRNA gene transcript is also called a "miRNA precursor," and is typically an RNA transcript of about 70-100 nucleotides in length. The miRNA precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miRNA gene transcript or "mature" miRNA.

The active 19-25 nucleotide RNA molecule can be obtained from the miRNA precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miRNA precursor. When a microRNA is referred to herein by name, the name corresponds to both the precursor and mature forms, unless otherwise indicated.

MicroRNA can be modified in accordance with the invention using any suitable chemical moiety including, for example, phosphorothioate, boranophosphate, 2'-O-methyl, 2'-fluoro, PEG, terminal inverted-dT base, locked nucleic acids (LNA), peptide nucleic acids (PNAs), 2'-fluoro N3-P5'-phosphoramidites, 1',5'-anhydrohexitol nucleic acids (HNAs), or combinations thereof. In particular embodiments, the miRNA is modified to include LNA. In a comparison of LNA-DNA-LNA gapmers with siRNAs, phosphorothioate and 2'-O-methyl RNA-DNA gapmers against expression of the vanilloid receptor subtype 1 (VR1) in Cos-7 cells, it was shown that LNA-DNA-LNA gapmers having a 5nt-8nt-5nt design were 175- and 550-fold superior in suppressing VR1 compared to isosequential phosphorothioate and 2'-Ome oligonucleotides respectively (Grunweller, et al. (2003) *NAR* 31:3185-93).

LNAs, often referred to as inaccessible RNA, are modified RNA nucleotides that can be placed either 5' or internally. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur, et al. (2006) *Biochemistry* 45(23):7347-55). LNA bases may be included in a backbone of LNA, 2'-O-methyl RNA, 2'-methoxyethyl RNA, or 2'-fluoro RNA. These molecules may utilize either a phosphodiester or phosphorothioate backbone.

The microRNAs of the invention and the sequences thereof are well-known in the art and can be found in the miRBase Sequence Database and Registry (Kozomara & Griffiths-Jones (2011) *Nucl. Acids Res.* 39:D152-7; Griffiths-Jones, et al. (2008) *Nucl. Acids Res.* 36:D154-8; and Griffiths-Jones (2004) *Nucl. Acids Res.* 32:D109-111. For example, human miR-25 (Gene ID 407014) has a precursor sequence of GGC CAG UGU UGA GAG GCG GAG ACU UGG GCA AUU GCU GGA CGC UGC CCU GGG CAU UGC ACU UGU CUC GGU CUG ACA GUG CCG GCC (SEQ ID NO:1) and mature sequence of CAU UGC ACU UGU CUC GGU CUG A (SEQ ID NO:2). Human miR-98 (Gene ID 407054) has a precursor sequence of AGG AUU CUG CUC AUG CCA GGG UGA GGU AGU AAG UUG UAU UGU UGU GGG GUA GGG AUA UUA GGC CCC AAU UAG AAG AUA ACU AUA CAA CUU ACU ACU UUC CCU GGU GUG UGG CAU AUU CA (SEQ ID NO:3) and a mature sequence of UGA GGU AGU AAG UUG UAU UGU U (SEQ ID NO:4). Human miR-185 (Gene ID 406961) has a precursor sequence of AGG GGG CGA GGG AUU GGA GAG AAA GGC AGU UCC UGA UGG UCC CCU CCC CAG GGG CUG GCU UUC CUC UGG UCC UUC CCU CCC A (SEQ ID NO:5) and mature sequence of UGG AGA GAA AGG CAG UUC CUG A (SEQ ID NO:6).

As demonstrated herein, administration of miR-25, miR-185, and miR-98 to Dgcr8$^{+/-}$ mice was sufficient to rescue aberrant LTP, a key cellular aspect of neural function. Therefore, the present includes methods for restoring, reversing or stabilizing age-dependent changes, in particular age-dependent decreases, in neural function and treating a learning or mental disorder by administering an effective amount of at least one of miR-25, miR-185 and miR-98 to a subject in need of such treatment.

As is known in the art, long-term potentiation or LTP is a long-lasting enhancement in signal transmission between two neurons that results from stimulating them synchronously (Cooke & Bliss (2006) *Brain* 129 (Pt 7): 1659-73). At a cellular level, LTP enhances synaptic transmission. It improves the ability of two neurons, one presynaptic and the other postsynaptic, to communicate with one another across a synapse. LTP is widely considered one of the major cellular mechanisms that underlies learning and memory (Cook & Bliss (2006) supra; Bliss & Collingridge (1993) *Nature* 361: 31-9) and is a key aspect of neural function.

As used herein, "treating" or "treatment" of a disease or disorder refers to arresting, reducing, ameliorating or delaying the onset of a disease, disorder, or at least one clinical symptom or physical parameter of a disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. As used herein, an "effective amount" of a miRNA gene product is an amount sufficient to measurably restore or reverse age-dependent decreases in neural function. Alternatively stated, an effective amount of a miRNA gene product measurably restores, reverses or stabilizes neural function to normal levels or levels observed younger subjects. One skilled in the art can readily determine an effective amount of a miRNA gene product to be administered to a given subject, by taking into account factors, such as the size and weight of the subject; health and sex of the subject; the route of administration; and whether the administration is regional or systemic. In addition, one skilled in the art can readily determine an appropriate dosage regimen for the administration of an isolated miRNA gene product to a given subject. For example, a miRNA gene product can be administered to the subject once (e.g., as a single injection or deposition). Alternatively, a miRNA gene product can be administered multiple times to a subject. Where a dosage regimen includes multiple administrations, it is understood that the effective amount of the miRNA gene product administered to the subject can include the total amount of gene product administered over the entire dosage regimen.

In some embodiments, the miRNA gene product is isolated. As used herein, an "isolated" miRNA gene product is one that is synthesized, or altered or removed from the natural state through human intervention. For example, a synthetic miRNA gene product, or a miRNA gene product partially or completely separated from the coexisting materials of its natural state, is considered to be "isolated." An isolated miRNA gene product can exist in a substantially-purified form, or can exist in a cell into which the miRNA gene product has been delivered. Thus, a miRNA gene product that is deliberately delivered to, or expressed in, a cell is considered an "isolated" miRNA gene product. A miRNA gene product produced inside a cell from a miRNA precursor molecule is also considered to be an "isolated" molecule. According to the invention, the isolated miRNA gene products described herein can be used for the manufacture of a medicament for treating a learning or mental disorder in a subject (e.g., a human).

Isolated miRNA gene products can be obtained using a number of standard techniques. For example, the miRNA gene products can be chemically synthesized or recombinantly produced using methods known in the art. In one embodiment, miRNA gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo.), Pierce Chemical (part of Perbio Science, Rockford, Ill.), Glen Research (Sterling, Va.), ChemGenes (Ashland, Mass.) and Cruachem (Glasgow, UK).

Alternatively, the miRNA gene products can be expressed from recombinant vectors, either individually or from the same or different vector. Recombinant vectors include circular or linear DNA plasmids and typically contain a suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also include inducible or regulatable promoters for expression of the miRNA gene products in brain cells.

The miRNA gene products that are expressed from recombinant plasmids can be isolated from cultured cell expression systems by standard techniques. The miRNA gene products that are expressed from recombinant plasmids can also be delivered to, and expressed directly in, the cells of interest.

In one embodiment, the miRNA gene products are expressed as RNA precursor molecules, and the precursor molecules are processed into the functional miRNA gene products by a suitable processing system, including, but not limited to, processing systems extant within, e.g., a hippocampal cell. Other suitable processing systems include, e.g., the in vitro *Drosophila* cell lysate system (e.g., as described in US 2002/0086356) and the *E. coli* RNAse III system (e.g., as described in US 2004/0014113).

Selection of plasmids suitable for expressing the miRNA gene products, methods for inserting nucleic acid sequences into the plasmid to express the gene products, and methods of delivering the recombinant plasmid to the cells of interest are within the skill in the art. See, for example, Zeng, et al. (2002) *Molecular Cell* 9:1327-1333; Tuschl (2002) *Nat. Biotechnol.* 20:446-448; Brummelkamp, et al. (2002) *Science.* 296:550-553; Miyagishi, et al. (2002) *Nat. Biotechnol.* 20:497-500; Paddison, et al. (2002) *Genes Dev.* 16:948-958; Lee, et al. (2002) *Nat. Biotechnol.* 20:500-505; and Paul, et al. (2002) *Nat. Biotechnol.* 20:505-508.

In one embodiment, a plasmid expressing the miRNA gene products includes a sequence encoding a miRNA precursor RNA under the control of the CMV intermediate-early promoter. As used herein, "under the control" of a promoter means that the nucleic acid sequences encoding the miRNA gene product are located 3' of the promoter, so that the promoter can initiate transcription of the miRNA gene product coding sequences.

The miRNA gene products can also be expressed from recombinant viral vectors. The RNA expressed from the recombinant viral vectors can either be isolated from cultured cell expression systems by standard techniques, or can be expressed directly in brain cells.

The recombinant viral vectors of the invention include sequences encoding the miRNA gene products and any suitable promoter for expressing the RNA sequences. Suitable promoters include, but are not limited to, the U6 or H1 RNA pol III promoter sequences, the cytomegalovirus promoters, or more particularly a neuron-specific promoter such as the Synapsin promoter. Selection of other suitable promoters is within the skill in the art.

Any viral vector capable of accepting the coding sequences for the miRNA gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, et al. (2002) *J. Virol.* 76:791-801.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995) *Gene Therap.* 2:301-310; Eglitis (1988) *Biotechniques* 6:608-614; Miller (1990) *Hum. Gene Therap.* 1:5-14; and Anderson (1998), *Nature* 392:25-30).

Particularly suitable viral vectors are those derived from AV and AAV. A suitable AV vector for expressing the miRNA gene products, a method for constructing the recombinant AV vector, and a method for delivering the vector into target cells, are described in Xia, et al. (2002) *Nat. Biotech.* 20:1006-1010. Suitable AAV vectors for expressing the miRNA gene products, methods for constructing the recombinant AAV vector, and methods for delivering the vectors into target cells are described in Samulski, et al. (1987) *J. Virol.* 61:3096-3101; Fisher, et al. (1996) *J. Virol.* 70:520-532; Samulski, et al. (1989) *J. Virol.* 63:3822-3826; U.S. Pat. No. 5,252,479; U.S. Pat. No. 5,139,941; WO 94/13788; and WO 93/24641. In one embodiment, the miRNA gene products are expressed from a recombinant AAV vector including neuron-specific Synapsin promoter.

Isolated miRNA gene products, either alone or in combination, can be formulated in pharmaceutical compositions suitable for administration to a subject in need of treatment. Such compositions typically contain from about 0.1 to 90% by weight (such as 1 to 20% or 1 to 10%) of the miRNA gene product in a pharmaceutically acceptable carrier. A pharmaceutically acceptable carrier is a material useful for the purpose of administering the medicament, which is preferably sterile and non-toxic, and can be solid, liquid, or gaseous materials, which is otherwise inert and medically acceptable, and is compatible with the active ingredients. A generally recognized compendium of methods and ingredients of pharmaceutical compositions is Remington: The Science and Practice of Pharmacy, Alfonso R. Gennaro, editor, 20th ed. Lippincott Williams & Wilkins: Philadelphia, Pa., 2000.

The pharmaceutical compositions (including isolated miRNA gene products or vectors encoding the same) can be administered to the subject being treated by any, or a combination, of several routes, such as oral, intravenous, transmucosal (e.g., nasal, vaginal, etc.), pulmonary, transdermal, ocular, buccal, sublingual, intraperitoneal, intrathecal, intramuscular, interstitial, intraventricular, intrathecal or long-term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the subject to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active agent(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like. As yet a further alternative, the instant miRNA gene products can be delivered by biodegradable polymer wafers, microspheres, or nanoparticles.

Subjects benefiting from treatment with instant methods include those having, those suspected of having or those predisposed to have (e.g., genetic predisposition) a learning disorder or mental disorder. Learning disorders include childhood learning disorders, wherein the subject has an impaired ability to learn. Such learning disorders can be diagnosed by using the DSM-IV criteria (APA, 1994, Diagnostic and Statistical Manual of Mental Disorders (Fourth Edition), Washington, D.C.). Mental disorders embraced by the present invention include, but are not limited to psychiatric diseases such as schizophrenia, Alzheimer's disease, bipolar disorder, schizoaffective disorder, 22q11 deletion syndrome, attention-deficit hyperactivity disorder, obsessive-compulsive disorder and autism spectrum disorder.

As used herein, the term "schizophrenia" refers to a psychiatric disorder that includes at least two of the following: delusions, hallucinations, disorganized speech, grossly disorganized or catatonic behavior, or negative symptoms. Subjects can be diagnosed as schizophrenic using the DSM-IV criteria.

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann, et al. (1984) *Neurology* 34:939-944). The patient's cognitive function can be assessed by the Alzheimer's Disease Assessment Scale-cognitive subscale (ADAS-cog; Rosen, et al. (1984) *Am. J. Psychiatry* 141:1356-1364).

Bipolar disorder, also known as manic depressive disorder, manic depression or bipolar affective disorder, is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and depression are present at the same time. These episodes are usually separated by periods of "normal" mood, but in some individuals, depression and mania may rapidly alternate, known as rapid cycling. Extreme manic episodes can sometimes lead to psychotic symptoms such as delusions and hallucinations. Subjects can be diagnosed as having bipolar disorder using the DSM-IV-TR criteria and the World Health Organization's International Statistical Classification of Diseases and Related Health Problems, the ICD-10.

Schizoaffective disorder is a psychiatric diagnosis that describes a mental disorder characterized by recurring episodes of mood disorder and psychosis. Distortions in perception alternate with and occur simultaneously with elevated or depressed mood. These perceptual distortions may affect all five senses, including sight, hearing, taste, smell and touch, but most commonly manifest as auditory hallucinations, paranoid or bizarre delusions, or disorganized speech and thinking with significant social or occupational dysfunction. Subjects can be diagnosed as having a schizoaffective disorder using the DSM-IV-TR criteria.

Characteristic signs and symptoms of 22q11 deletion syndrome may include birth defects such as congenital heart disease, defects in the palate, most commonly related to neuromuscular problems with closure (velo-pharyngeal insufficiency), learning disabilities, mild differences in facial features, and recurrent infections. 22q11 deletion syndrome may be first spotted when an affected newborn has heart defects or convulsions from hypocalcemia due to malfunctioning the parathyroid glands and low levels of parathyroid hormone (parathormone). Affected individuals may also have any other kind of birth defect including kidney abnormalities and significant feeding difficulties as babies. Autoimmune disorders such as hypothyroidism and hypoparathyroidism or thrombocytopenia (low platelet levels), and psychiatric illnesses are common late-occurring features. Diagnosis of 22q11 deletion syndrome is typically determined by the presence of the 22q11.2 microdeletion.

The term "attention-deficit hyperactivity disorder attention deficit disorder," as used herein, refers to a disorder that is most commonly exhibited by children and which can be characterized by increased motor activity and a decreased attention span. The DSM-IV criteria can be used to diagnose attention deficit disorder.

Obsessive-compulsive disorder (OCD) is a mental disorder characterized by intrusive thoughts that produce anxiety, by repetitive behaviors aimed at reducing anxiety, or by combinations of such thoughts (obsessions) and behaviors (compulsions). The symptoms of this anxiety disorder range from repetitive hand-washing and extensive hoarding to preoccupation with sexual, religious, or aggressive impulses as well as corrections of minor things. These symptoms can be alienating and time-consuming, and often cause severe emotional and economic loss. Although the acts of those who have OCD may appear paranoid and come across to others as psychotic, OCD sufferers often recognize their thoughts and subsequent actions as irrational, and they may become further distressed by this realization.

As used herein, the term "autism spectrum disorder" refers to a spectrum of psychological conditions characterized by widespread abnormalities of social interactions and communication, as well as severely restricted interests and highly repetitive behavior. Subjects with autism experience mental introversion characterized by morbid self-absorption, social failure, language delay, and stereotyped behavior. The three main forms of ASD are Autism, Asperger syndrome, Pervasive Developmental Disorder Not Otherwise Specified (PDD-NOS), sometimes called atypical autism. Patients can be diagnosed as suffering from autism by using the DSM-IV criteria.

Subjects to be treated in accordance with the instant method can be provided with an effective amount of a miRNA gene product as described herein. Where appropriate, a pharmaceutical composition containing a miRNA gene product can be administered to a subject suffering from learning or mental disorder along with, or in sequence with, an art-known drug for treating the learning or mental disorder. For example, art-known drugs for treating schizophrenia, include olanzapine, clozapine, haloperidol, and the like. Similarly, a miRNA gene product can be used in combination with, or in sequence with, other art-known antipsychotics (e.g., "typical," "atypical," and depot antipsychotics for treating schizophrenia and other psychotic conditions), psychostimulants (for treating attention deficit disorder or learning disorders), or Alzheimer's disease therapeutics (for treating Alzheimer's disease). Such pharmaceutical compositions are included within the invention. In general, the antipsychotic, psychostimulant, or Alzheimer's disease therapeutic typically is administered at a dosage of 0.25-5000 mg/d (e.g., 5-1000 mg/d)). "Typical" antipsychotics are conventional antipsychotics such as phenothiazine, butryophenones, thioxantheses, dibenzoxazepines, dihydroindolones, and diphenylbutylpiperidines. "Atypical" antipsychotics are a new generation of antipsychotics which generally act on the dopamine $D_2$ and $5HT_2$ serotonin receptor and have high levels of efficacy and a benign extrapyramidal symptom side effect profile. Examples of typical antipsychotics include Chlorpromazine, Thioridazine, Mesoridazine, Fluphenazine, Perphenazine, Trifluoperazine, Thiothixene, Haloperidol, Loxapine, Molindone, Acetophenazine, Droperidol, Pimozide. Examples of atypical antipsychotics include Clozapine, Risperidone, Olanzapine, and Quetiapine. Depot antipsychotics also can be used, e.g., Haloperidol decanoate, Fluphenazine decanoate, and Fluphenazine enanthate. Additional antipsychotics include Butaperazine, Carphenazine, Remoxipride, Piperacetazine, Sulpiride, and Ziprasidone. Psychostimulants that are particularly useful for treating attention deficit disorder include Dextroamphetamine, Methamphetamine, Methylphenidate, and Pemoline. Examples of Alzheimer's disease therapeutics that can be used in the invention include Donepezil and Tacrine. Thus, the invention also provides pharmaceutical compositions that contain one or more miRNA gene products along with an antipsychotic, psychostimulant, or Alzheimer's disease therapeutic.

In addition to, or as an alternative to, conventional methods of diagnosing a subject for a learning disorder or mental disorder, the present invention also includes a method for diagnosing an increased susceptibility to developing a learning or mental disorder based upon the levels of one or more of miR-25, miR-98 or miR-185. In accordance with the diagnostic method of the invention, a biological sample is obtained from a subject to be tested, and the level of the miRNA gene product in said sample is measured with an miRNA-specific probe and compared to a control, wherein a reduced or decreased level of the miRNA gene product as compared to the control is diagnostic for an increased susceptibility to developing a learning or mental disorder. As used herein, a "subject" can be any mammal that has, or is suspected of having, a learning or mental disorder. In a preferred embodiment, the subject is a human who has, or is suspected of having, a learning or mental disorder.

Levels of miRNA expression can be determined using oligonucleotides that specifically hybridize with the miRNA of interest in routine methods for detecting nucleic acids in a sample, e.g., northern blot analysis, qRT-PCR, in situ hybridization and the like. To detect the level of miRNA, the method of the invention employs oligonucleotides, e.g. primers or probes. The term "probe" refers to a defined oligonucleotide or a nucleic acid molecule used to detect a target miRNA nucleic acid molecule by hybridization, in particular in situ hybridization or northern blot analysis. In this respect, a probe bears a complementary sequence to the miRNA sequence of interest. Like a probe, a primer bears a complementary sequence to the miRNA sequence of interest and typically refers to an oligonucleotide or a nucleic acid molecule used to detect a target miRNA nucleic acid molecule by amplification, e.g., PCR. Probes and primers of the invention can be single-stranded DNA, partially double-stranded DNA, RNA or a combination of DNA and RNA.

In particular embodiments, the probe or primer hybridizes with a human miR-25 sequence of SEQ ID NO:1 and/or SEQ ID NO:2. An example of a reverse transcriptase primer for human miR-25 is 5'-GCA TAC TCC GAC CGT TAC TTC AGA CCG-3' (SEQ ID NO:7), whereas reverse and forward PCR primers for amplifying miR-25 have the sequences 5'-GGT GCC ATT GCA CTT GTC TC-3' (SEQ ID NO:8) and 5'-TCA GCA TAC TCC GAC CGT TAC T-3' (SEQ ID NO:9), respectively. In some embodiments, the probe or primer has a nucleotide sequence of SEQ ID NO:35 or a fragment thereof that can hybridize under stringent conditions, and/or has an identity of at least 80% to any of this sequence.

In other embodiments, the probe or primer hybridizes with a human miR-98 sequence of SEQ ID NO:3 and/or SEQ ID NO:4. An example of a reverse transcriptase primer for human miR-98 is 5'-GGC GTA ATA ATC GCT CCA TTC AAC AAT ACA A-3' (SEQ ID NO:10), whereas reverse and forward PCR primers for amplifying miR-98 have the sequences 5'-CGC AAG AAG TGA GGT AGT AAG TTG-3' (SEQ ID NO:11) and 5'-CGG CGT AAT AAT CGC TCC ATT C-3' (SEQ ID NO:12), respectively. In some embodiments, the probe or primer has a nucleotide sequence of SEQ ID NO:28 or a fragment thereof that can hybridize under stringent conditions, and/or has an identity of at least 80% to any of this sequence.

In yet another embodiment, the probe or primer hybridizes with a human miR-185 sequence of SEQ ID NO:5 and/or SEQ ID NO:6. Examples of forward and reverse PCR primers for amplifying miR-185 have the sequences 5'-CAA TGG AGA GAA AGG CAG TTC C-3' (SEQ ID NO:13) and 5'-AAT CCA TGA GAG ATC CCT ACC G-3' (SEQ ID NO:14), respectively. In some embodiments, the probe or primer has a nucleotide sequence of SEQ ID NO:15 or a fragment thereof that can hybridize under stringent conditions, and/or has an identity of at least 80% to any of this sequence.

In some embodiments, the probe or primer of the invention is synthesized or produced with conventional oligonucleotides. In other embodiments, the probe or primer is modified to include chemical modifications. If present, chemical modifications of a probe or primer can include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylammonium) propyl]carboxyamide)-2'-deoxyuridine chloride, 5-(N-napthylmethylcarboxyamide)-2'-deoxyuridine, 5-(Imidazolylethyl)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, backbone modifications, methylations, unusual base-pairing combinations such as the isobases isocytidine and isoguanidine, and the like.

In one embodiment, 5-position pyrimidine modifications refer to pyrimidines with a modification at the C-5 position. Examples of a C-5 modified pyrimidine include those described in U.S. Pat. Nos. 5,719,273 and 5,945,527. Examples of a C-5 modification include substitution of deoxyuridine at the C-5 position with a substituent selected from benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) In this respect, representative C-5 modified pyrimidines include 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU) and 5-(N-napthylmethylcarboxyamide)-2'-deoxyuridine (NapdU).

Modified probes or primers of the invention include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). In particular embodiments, a modified probe or primer of the invention contains at least one nucleoside analog, e.g., a locked nucleic acid (LNA). The synthesis and preparation of LNA monomers adenine, cytosine, guanine, 5-methyl-cytosine, thymine and uracil, along with their oligomerization, and nucleic acid recognition properties have been described (Koshkin, et al. (1998) *Tetrahedron* 54:3607-3630). LNAs and preparation thereof are also described in WO 98/39352 and WO 99/14226.

Other modifications include 3' and 5' modifications, such as capping. Further, any of the hydroxyl groups ordinarily present in a sugar may be replaced by a phosphonate group or a phosphate group; protected by any suitable protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (C1-C20) optionally containing an ether (—O—) linkage, aryl, alkenyl, cycloalkyl, cycloalkenyl or araldyl. Not all linkages in a probe need be identical. Substitution of analogous forms of sugars, purines, and pyrimidines can be advantageous in designing a final product, as can alternative backbone structures like a polyamide backbone, for example.

If present, a modification to the nucleotide structure of a probe or primer may be imparted before or after assembly of the probe or primer. A sequence of nucleotides may be interrupted by non-nucleotide components. A probe or primer may be further modified after polymerization, such as by conjugation with a labeling component.

In accordance with the present method, a probe can be detected with a label or tag or otherwise modified to facilitate detection. A label or a tag is an entity making it possible to identify a compound to which it is associated. It is within the scope of the present invention to employ probes that are labeled or tagged by any means known in the art such as, but not limited to, radioactive labeling, affinity labeling (e.g., with a hapten and its associated antibody), fluorescent labeling and enzymatic labeling. Furthermore, the probe may be immobilized to facilitate detection. In particular embodiments, a hapten is incorporated into the probe of the invention. Haptens commonly employed in labeling applications include fluorescein (e.g., 5- or 6-carboxy-fluorescein, FAM), biotin, digoxigenin (DIG), 5-bromo-2-deoxyuridine (BrdU) and dinitrophenol. Probe synthesis and hapten incorporation are routinely practiced in the art and any suitable method can be employed. See, e.g., Luehrsen, et al. (2000) *J. Histochem. Cytochem.* 48:133-145.

Detection of probes with labels is routinely practiced in the art and any suitable method can be employed. In particular embodiments, the probe contains a hapten that is detectable using an immunoassay. Accordingly, certain embodiments of this invention include the use of an anti-hapten antibody. In this respect, binding of the probe to the miRNA can be detected by contacting the hapten with an anti-hapten antibody, contacting the anti-hapten antibody with a secondary antibody reagent, and detecting the secondary antibody reagent by routine methods as described herein. For the purposes of the present invention, a secondary antibody reagent is composed of an antibody covalently linked to a protein that provides for a detectable signal. Suitable detectable proteins include, but are not limited to, fluorescent proteins, chromogenic proteins, and enzymes that catalyze the production of a product that is luminescent, fluorescent, or colored (e.g., β-galactosidase, luciferase, horse radish peroxidase, alkaline phosphatase, etc.). Suitable fluorescent proteins include, but are not limited to, green fluorescent protein (GFP; Chalfie, et al. (1994) *Science* 263(5148):802-805); enhanced GFP (EGFP; Clontech Laboratories, Inc.); blue fluorescent protein (BFP; Stauber (1998) *Biotechniques* 24(3):462-471; Heim & Tsien (1996) *Curr. Biol.* 6:178-182); enhanced yellow fluorescent protein (EYFP; Clontech Laboratories, Inc.); and the like. Secondary antibodies linked to various enzymes (i.e., enzyme-conjugated) are commercially available from, for example, Sigma and Amersham Life Sciences (Arlington Heights, Ill.). In certain embodiments, horseradish peroxidase-conjugated secondary antibodies are used in the detection steps of the instant method. In particular embodiments, the invention embraces the use of horseradish peroxidase-mediated tyramide signal amplification (TSA) to enhance detection.

As is known in the art, there are a variety of luminescent, fluorescent, or colored substrates for detecting the activity of enzyme-conjugated secondary antibodies, e.g., by microscopy. For example, horseradish peroxidase-labeled secondary antibody is readily detected with 3,3'-Diaminobenzidine (DAB) and as alkaline phosphatase labeled secondary antibody is readily detected with 5-bromo-4-chloro-3'-indolylphosphate p-toluidine salt (BCIP) and nitro-blue tetrazolium chloride (NBT), both of which are commercially available from a variety of sources (e.g., Pierce Chemical Co., Rockford, Ill.). The enzymatic reaction forms an insoluble colored product wherever antigen-antibody complexes occur.

The level of at least one of miR-25, miR-98 or miR-185 can be measured in cells of a biological sample obtained from the subject and compared to a control. For example, a tissue sample can be removed from a subject suspected of having, or susceptible to developing, a learning or mental disorder by conventional biopsy techniques. A corresponding control tissue sample, or a control reference sample, can be obtained from unaffected tissues of the subject, from a normal human individual or population of normal individuals, or from cultured cells corresponding to the majority of cells in the subject's sample. The control tissue sample is then processed along with the sample from the subject, so that the levels of miRNA gene product produced from a given miRNA gene in cells from the subject's sample can be compared to the corresponding miRNA gene product levels from cells of the control sample. Alternatively, a reference sample can be obtained and processed separately (e.g., at a different time) from the test sample and the level of a miRNA gene product produced from a given miRNA gene in cells from the test sample can be compared to the corresponding miRNA gene product level from the reference sample.

In one embodiment, the level of the at least one of miR-25, miR-98 or miR-185 in the test sample is less than the level of the corresponding miRNA gene product in the control sample (i.e., expression of the miRNA gene product is "down-regulated"). As used herein, expression of a miRNA gene product is "down-regulated" when the amount of miRNA gene product in a cell or tissue sample from a subject is less than the amount of the same gene product in a control cell or tissue sample. The relative miRNA gene expression in the control and normal samples can be determined with respect to one or more RNA expression standards. The standards can include, for example, a zero miRNA gene expression level, the miRNA gene expression level in a standard cell line, the miRNA gene expression level in unaffected tissues of the subject, or the average level of miRNA gene expression previously obtained for a population of normal human controls. A decrease in the level of a miRNA gene product in the sample obtained from the subject, relative to the level of a corresponding miRNA gene product in a control sample, is then used to diagnose a subject as being susceptible to, or having, a learning or mental disorder. In this respect, the diagnostic methods of the invention can be used in the initial determination of whether a subject has a learning or mental disorder or in the confirmation of a diagnosis based upon conventional behavioral or clinical analysis. Subjects benefiting from the instant diagnostic methods include those suspected of having, or those predisposed (e.g., based upon heredity) to have a learning or mental disorder.

As with the method of treatment, learning or mental disorders that can be diagnosed in accordance with the instant diagnostic methods include, but are not limited to, having, suspected of having or those predisposed to have schizophrenia, Alzheimer's disease, bipolar disorder, schizoaffective disorder, 22q11 deletion syndrome, attention-deficit hyperactivity disorder, obsessive-compulsive disorder or autism spectrum disorder.

The invention is described in greater detail by the following non-limiting examples.

Example 1

Materials and Methods

Animals.

Young (8-10 weeks) and mature (16-20 weeks) mice of both sexes were used for all experiments except the microarray experiments, for which only male mice were used. Dgcr8$^{+/-}$ mice were generated from the XH157 ES cell line (Bay Genomics) as previously described (Stark, et al. (2008) *Nat. Genet.* 40:751-60; Schofield, et al. (2011) *Neural Dev.* 6:11). Zdhhc8$^{+/-}$ mice were generated from the IST14452C2 ES cell line (TIGM), which contains a gene-trap insertion downstream of the first exon. To expand the colony, Dgcr8$^{+/-}$ and Zdhhc8+/− mice harboring the disrupted alleles were bred to C57BL/6J mice. Production and genotyping of Df(16)1/+ (Lindsay, et al. (1999) *Nature* 401:379-383), Df(16)2/+ (Lindsay, et al. (2001) *Nature* 410:97-101), Znf74l-Ctp/+ (Kimber, et al. (1999) *Hum. Mol. Genet.* 8:2229-2237), Prodh+/− (Gogos, et al. (1999) *Nat. Genet.* 21:434-439), Comt+/− (Gogos, et al. (1998) *Proc. Natl. Acad. Sci. USA* 95:9991-9996), and Rtn4r+/− (Kim, et al. (2004) *Neuron* 44:439-451) mice have been previously described. All mouse strains in this study were back-crossed onto the C57BL/6J genetic background for at least six generations.

Electrophysiology.

Acute transverse hippocampal slices (400 μm) were prepared according to known methods (Earls, et al. (2010) *J. Neurosci.* 30:15843-15855). Briefly, mouse brains were quickly removed and placed in cold (4° C.) dissecting artificial CSF (ACSF) containing 125 mM choline-Cl, 2.5 mM KCl, 0.4 mM $CaCl_2$, 6 mM $MgCl_2$, 1.25 mM $NaH_2PO_4$, 26 mM $NaHCO_3$, and 20 mM glucose (285-295 mOsm), under 95% $O_2$/5% $CO_2$. After dissection, slices were incubated for 1 hour in ACSF containing 125 mM NaCl, 2.5 mM KCl, 2 mM $CaCl_2$, 2 mM $MgCl_2$, 1.25 mM $NaH_2PO_4$, 26 mM $NaHCO_3$, and 10 mM glucose (285-295 mOsm), under 95% $O_2$/5% $CO_2$ at room temperature, and then transferred into submerged recording chambers and superfused (2-3 ml/min) with warm (30-32° C.) ACSF. Field recordings were performed using a setup with eight submerged recording chambers (Campden Instruments). Recordings in each chamber were performed independently. Field EPSPs (fEPSPs) from the CA1 stratum radiatum were recorded by using an extracellular glass pipette (3-5 MΩ) filled with ACSF. Schaffer collateral fibers in the stratum radiatum were stimulated with a bipolar tungsten electrode placed 200-300 μm away from the recording pipette. Stimulation intensities were chosen to produce an fEPSP with a 0.5 V/s slope. LTP was induced by three periods of 200 Hz tetanization delivered every 5 minutes. Each period of tetanization included 10 trains of 200 Hz stimulation delivered at the same intensity for 200 ms (40 stimulations) every 5 seconds.

Western Blot Analysis.

Western blots were performed according to known methods (Earls, et al. (2010) supra). For human brain tissue, dissected samples arrived from brain banks frozen on dry ice. Mouse tissue was dissected at 4° C. and prepared either as whole-tissue lysates or as crude P2 synaptosomal fractions. Synaptosomes were prepared using established methods (Gray & Whittaker (1962) *J. Anat.* 96:79-88). In brief, tissue was homogenized in 10 mM HEPES (pH 7.4)/0.32 M sucrose using a motorized glass-TEFLON homogenizer. To separate the P2 synaptosomal fraction, the homogenate was spun for 5 minutes at 800×g; the supernatant from three successive spins was then centrifuged for 20 minutes at 12,000×g. Tissue or synaptosomal pellets were lysed by freezing and thawing, subsequent syringe passage in ice-cold radioimmunoprecipitation assay buffer (50 mM Tris-HCl (pH 7.4), 1% NP-40, 0.25% sodium deoxycholate, 150 mM NaCl, 1 mM EDTA, and protease inhibitor cocktail tablets (Roche), and finally brief sonication. Concentrations of protein lysates were determined by the BCA assay (Thermo Scientific). A 25 μg sample of each protein extract was electrophoresed on a 10% SDS-PAGE gel, and protein was transferred onto polyvinylidene difluoride membranes (Invitrogen). The primary antibodies used were goat anti-SERCA2 (1:250, sc-8095; Santa Cruz Biotechnology) and mouse anti-β-actin (1:10000, A5316; Sigma-Aldrich). SERCA and β-actin western blots were probed with anti-mouse (1:5000) and anti-goat (1:5000) secondary antibodies conjugated to IR dye 680 or 800 (LI-COR Biosciences). These blots were imaged and quantified using the ODYSSEY infrared imaging system (LI-COR Biosciences).

MicroRNA Microarray.

Total RNA was isolated from 4-month-old male wild-type (WT) and Df(16)1/+ hippocampi using the MIRVANA RNA Isolation kit (Ambion). A mouse miRNA microarray (Agilent-029298; Agilent Technologies) was composed of probes for 690 mouse miRNAs from the Sanger miRBase (release 14.0) was designed and manufactured by Agilent Technologies. Array hybridization was performed according to the manufacturer's recommended protocols. In brief, total RNA was labeled using the Agilent miRNA labeling kit. Hybridization was performed in an Agilent oven at 55° C. for 20 hours at 20 rpm, followed by standard wash procedures. The microarray was then scanned in an Agilent scanner at 5 μm resolution, and the array data were extracted using the default miRNA settings of Agilent Feature Extraction Software (v10.5.1.1) with the miR__105_Jan09 protocol. Signal intensity was normalized at the 80th percentile, scaled across the sample set, and log 2 transformed. The minimum detecting miRNA expression signal was set at a threshold greater than the 99th percentile of those from the negative-control probes. A p value was calculated using a t test of samples from two different experimental conditions.

Quantitative Real-Time PCR.

Total RNA (1 μg) was polyadenylated and reverse-transcribed using an oligo-dT primer with an attached universal sequence tag according to the miRNA First-Strand cDNA Synthesis kit (Stratagene/Agilent). The qPCR was then performed using SYBR green (Applied Biosystems); a forward primer specific to the miRNA of interest (5'→3'): mmu-miR185 (TGG AGA GAA AGG CAG TTC CT, SEQ ID NO:15), mmu-miR-299* (TGG TTT ACC GTC CCA C, SEQ ID NO:16), mmu-miR-337-3p (TTC AGC TCC TAT ATG ATG, SEQ ID NO:17), mmu-miR-411 (TAG TAG ACC GTA TAG CGT A, SEQ ID NO:18), mmu-miR-411* (TAT GTA ACA CGG TCC ACT A, SEQ ID NO:19), mmu-miR-874 (CTG GCC CGA GGG ACC, SEQ ID NO:20), mmu-miR-374 (ATA TAA TAC AAC CTG CTA AG, SEQ ID NO:21), mmu-miR-379 (TGG TAG ACT ATG GAA CGT A, SEQ ID NO:22), mmu-miR-337-5p (GAA CGG CGT CAT GCA GGA G, SEQ ID NO:23), mmu-miR-329 (AAC ACA CCC AGC TAA CCT TT, SEQ ID NO:24), mmu-miR-674* (CAC AGC TCC CAT CTC AGA AC, SEQ ID NO:25), mmu-miR-323-3p (TAC AGT TGT TCA ACC AGT TA, SEQ ID NO:26), mmu-miR-582-5p (TAC AGT TGT TCA ACC AGT TA, SEQ ID NO:27), mmu-miR-98 (TGA GGT AGT AAG TTG TAT TG, SEQ ID NO:28), mmu-miR-672 (TGA GGT TGG TGT ACT GTG TGT, SEQ ID NO:29), mmu-miR-421 (ATC AAC AGA CAT TAA TTG GGC, SEQ ID NO:30), mmu-miR-409-5p (AGG TTA CCC GAG CAA CTT TGC, SEQ ID NO:31), mmu-miR-872 (AAG GTT ACT TGT TAG TTC A, SEQ ID NO:32), mmu-miR-532-3p (CCT CCC ACA CCC AAG GCT TG, SEQ ID NO:33), mmu-miR-425 (AAT GAC ACG ATC ACT CCC GTT, SEQ ID NO:34), mmu-miR-25 (CAT TGC ACT TGT CTC GGT CT, SEQ ID NO:35), U6snRNA_Forward (CGC TTC GGC AGC ACA TAT AC, SEQ ID NO:36), U6snRNA_Reverse (TTC ACG AAT TTG CGT GTC AT, SEQ ID NO:37), and a universal reverse primer specific to the sequence tag (miRNA First-Strand cDNA Synthesis kit; Stratagene/Agilent). qPCR was performed in an Applied Biosystems 7900HT Fast Real-Time PCR System using the following cycling parameters: 55° C. (2 minutes), 95° C. (10 minutes), 40 cycles of 95° C. (15 seconds), 60° C. (30 seconds), and 72° C. (20 seconds). miRNA concentrations were calculated using cycle threshold values and a standard curve made from serial dilutions of wild-type cDNA samples (dilutions: 1:3, 1:9, 1:27, 1:81, 1:243, 0). The control, U6 snRNA (primers based upon those described in Thomson, et al. (2006) *Genes Dev.* 20:2202-2207), showed no difference between wild-type and Df(16) 1/+ samples. Therefore, all miRNA concentrations were normalized to the U6 level for a given animal. All PCR experiments were conducted in duplicate. PCR products were separated in a 5% polyacrylamide gel to confirm the presence of a single band of the expected size, and PCR products were cloned and sequenced to confirm the identity of each miRNA. Mature forms of miRNAs produced a single band ~80 bp in size in agreement with estimations (22 bp miRNA+polyA tail of varying size+32 bp universal tag sequence).

In Vivo Viral Injections. Adeno-associated viruses (AAVs) were prepared by cloning chimeric hairpins of them iRNAs of interest with hsa-miR-30a into the pAAV-6P-SEWB vector (Christensen, et al. (2010) *Front. Neural Circuits* 3:16). The following primers were used: ChimericmiR185up1 (GTA CAG CTG TTG ACA GTG AGC GAC TGG AGA GAA AGG CAG TTC CTG ATG TGA A, SEQ ID NO:38), ChimericmiR185up2 (GCC ACA GAT GGT CAG GAA CTC TTT CTC TCC AGC TGC CTA CTG CCT CGG AA, SEQ ID NO:39), ChimericmiR185low1 (CCA TCT GTG GCT TCA CAT CAG GAA CTG CCT TTC TCT CCA GTC GCT CAC TGT CAA CAG CT, SEQ ID NO:40), ChimericmiRl85low2 (AGC TTT CCG AGG CAG TAG GCA GCT GGA GAG AAA GAG TTC CTG A, SEQ ID NO:41), ChimericmiR25up1 (GTA CAG CTG TTG ACA GTG AGC GAC AGG CGG AGA CTT GGG CAA TTG CTG TGA A, SEQ ID NO:42), ChimericmiR25up2 (GCC ACA GAT GGG CAA TTG CCA GTC TCC GCC TGC TGC CTA CTG CCT CGG AA, SEQ ID NO:43), ChimericmiR25low1 (CCA TCT GTG GCT TCA CAG CAA TTG CCC AAG TCT CCG CCT GTC GCT CAC TGT CAA CAG CT, SEQ ID N0:44), and ChimericmiR25low2 (AGC TTT CCG AGG CAG TAG GCA GCA GGC GGA GAC TGG CAA TTG C, SEQ ID N0:45).

Viruses were prepared by cotransfecting each plasmid into HEK293 cells with both pDp1 and pDp2 helper plasmids. AAVs were then harvested and purified according to established methods (Zolotukhin, et al. (1999) *Gene Ther.* 6:973-985). Titers were in the range of $10^{11}$ TU/ml. Anesthesia in mice (10 weeks of age) was induced with 2-2.50 isoflurane (in 100% $O_2$). Anesthesia was maintained during surgery using 1.5% isoflurane. A 1/32-G cannula was inserted into the brain to deliver 2 µl AAV-miRNA or AAV-empty in three locations centered on the CA3 region of the hippocampus (AP: −1.8 mm; L: ±2.4 mm; V: −2.0 mm). AAV-miRNA was injected into one hemisphere, and green fluorescent protein (GFP)-only control AAV was injected into the contralateral hemisphere. Following AAV injections, incisions were sutured, and mice were allowed to recover and were then returned to holding cages. Electrophysiological and imaging experiments in hippocampal slices from these mice were performed 6-8 weeks after AAV injections.

Spatial Memory Testing.

Spatial memory was tested in the Morris water maze (Earls, et al. (2010) supra). Briefly, animals learned to find a platform hidden under water clouded with nontoxic, water-based paint. The platform was located in the same "training quadrant" of the pool, and mice learned to locate its position using the standard version of the Morris water maze spatial learning task for 10 successive days. A spatial memory probe trial was administered on the day after the completion of spatial learning. With the platform removed, animals received a single 1 minute trial in which they tried to find the escape platform in the training quadrant. This trial started from the point that was the farthest from the platform's location on the previous training day. The overall path length was measured for each mouse, and the relative path length for each quadrant was calculated.

Human Brain Tissue.

Postmortem samples of human prefrontal cortex were obtained from the Alzheimer Disease and Schizophrenia Brain Bank (Mount Sinai School of Medicine, New York, N.Y.). Samples from 17 patients with schizophrenia and 22 unaffected controls were used. Postmortem samples of human hippocampus were obtained from the Harvard Brain Tissue Resource Center (McLean Hospital, Belmont, Mass.). Samples from five patients with schizophrenia and six age-matched unaffected controls (all males) were used.

Drugs.

Drugs were purchased from Sigma-Aldrich, except thapsigargin, which was purchased from Tocris Bioscience.

Statistical Analyses.

All data are represented as mean±SEM. Statistical analyses for all experiments were performed using nonparametric Mann-Whitney rank sum, Wilcoxon signed rank, or t tests measured in Sigma Stat (Systat Software). Kruskal-Wallis one-way ANOVA by ranks was used to compare >2 independent groups.

Example 2

Age-Dependent LTP Increase in $Dgcr8^{+/-}$ Mice

In Df(16)1/+ mice, LTP of synaptic transmission measured at excitatory hippocampal synapses between CA3 and CA1 pyramidal neurons (CA3-CA1 synapses) is increased in mature (16-20 weeks) but not young (8-10 weeks) animals (Earls, et al. (2010) supra). LTP was >200% higher in mature Df(16)1/+ mice than WT littermates, whereas basal synaptic transmission at CA3-CA1 synapses in Df(16)1/+ mice was normal.

To narrow the location of genes involved in the LTP phenotype, mice that carry smaller hemizygous subdeletions within the Df(16)1 region were analyzed (Kimber, et al. (1999) *Hum. Mol. Genet.* 8:2229; Lindsay, et al. (2001) *Nature* 410:97). Basal synaptic transmission and LTP of field excitatory postsynaptic potentials (fEPSPs) was tested in acute hippocampal slices from Df(16)2/+ mice, which carry a hemizygous deletion of genes at the proximal end of the Df(16)1 region (Es2el-Trxr2). As in Df(16)1/+ mice, LTP was elevated in Df(16)2/+ animals in an age-dependent fashion.

In young animals, the increase in fEPSP slope (measure of LTP) quantified 6 hours after tetanization of Schaffer collaterals was not significantly different between Df(16)2/+ and wild-type littermates (Df(16)2/+: 20 slices, 4 mice; wild-type: 23 slices, 5 mice; p=0.238). However, in mature Df(16) 2/+ mice, LTP was higher than in wild-type littermates (Df (16)2/+: 22 slices, 6 mice; wild-type: 27 slices, 7 mice; p=0.006). On average, LTP in Df(16)2/+ mice was ~100% higher than that in wild-type littermates.

As in Df(16)1/+ mice, basal synaptic transmission was normal in both young and mature Df(16)2/+ mice. Thus, the input-output relationship between fEPSPs and stimulation intensity was comparable in young and mature wild-type and Df(16)2/+ mice (young Df(16)2/+: 20 slices, 4 mice; young wild-type: 23 slices, 5 mice, p>0.05; mature Df(16)2/+: 22 slices, 6 mice; mature wild-type: 27 slices, 7 mice, p>0.05).

Changes in LTP are often associated with changes in learning and memory. The substantial increase in LTP at CA3-CA1 synapses in mature Df(16)1/+ mice is accompanied by a mild deficit in hippocampus-dependent spatial memory, as measured in the Morris water maze task (Earls, et al. (2010) supra). In mature Df(16)2/+ mice, however, spatial memory tested in the Morris water maze task was normal (27 Df(16) 2/+ and 26 wild-type mice, p=0.875), indicating that additional genetic factors are required for the full effect on learning and memory.

To further narrow the LTP-critical region, LTP was measured in Znf74l-Ctp/+ mice (Kimber, et al. (1999) supra), which carry a hemizygous, 150-kilobase subdeletion that includes the three most proximal Df(16)2 genes, Es2el, Gscl, and Ctp. LTP was normal in mature Znf74l-Ctp/+ mice compared with wild-type littermates, indicating that Es2el, Gscl, and Ctp do not contribute to the phenotype observed in Df(16) 2/+ mice. Among the remaining genes in the Df(16)2 region, five have been previously implicated in the pathogenesis of 22q11DS and schizophrenia. To test their contribution to age-dependent LTP, mice deficient for those genes were analyzed. These included Zdhhc8$^{+/-}$ and Dgcr8$^{+/-}$ mice, which were produced during this study, and Comt$^{+/-}$ (Gogos, et al. (1998) Proc. Natl. Acad. Sci. USA 95:9991), Prodh$^{+/-}$ (Gogos, et al. (1999) Nat. Genet. 21:434), and Rtn4r$^{+/-}$ (Kim, et al. (2004) Neuron 44:439) mice. A comparison of LTP between the mutants and wild-type littermates from each mutant line at 16 weeks of age revealed an LTP increase only in Dgcr8$^{+/-}$ mice. Similar to Df(16)2/+ mice, the LTP increase in Dgcr8$^{+/-}$ mutants was age-dependent; there was no increase in LTP in wild-type littermates in 8- to 10-week-old animals (Dgcr8$^{+/-}$: 31 slices, 7 mice; wild-type: 39 slices, 7 mice, p=0.850). However, mature Dgcr8$^{+/-}$ mice demonstrated enhanced LTP equivalent to that of Df(16)2/+ mutants (Dgcr8$^{+/-}$: 29 slices, 6 mice; wild-type: 32 slices, 7 mice, p<0.001). Input-output coupling did not differ between young and mature Dgcr8$^{+/-}$ and wild-type littermates, indicating that hemizygous deletion of Dgcr8 does not affect basal synaptic transmission. These results implicate Dgcr8 as the gene from the Df(16)2 region that is responsible for the observed abnormalities in synaptic plasticity.

Example 3

Age-Dependent Upregulation of SERCA2 in the Dgcr8$^{+/-}$ Hippocampus

Age-dependent overexpression of SERCA2 is crucial for the LTP increase observed in Df(16)1/+ mice (Earls, et al. (2010) supra). SERCA2 is increased in the hippocampus of mature but not young Df(16)1/+ mice, and SERCA inhibitors rescue the LTP increase in mature Df(16)1/+ mice (Earls, et al. (2010) supra). Therefore, SERCA2 protein levels were determined in the hippocampus of young and mature Dgcr8$^{+/-}$ mice. Although no difference in SERCA2 levels was observed between Dgcr8$^{+/-}$ and wild-type whole-hippocampus extracts, SERCA2 protein levels in synaptosomal preparations from the hippocampus of mature Dgcr8$^{+/-}$ mice was significantly elevated compared with that in wild-type littermates (p<0.001). In contrast, this synaptic increase in SERCA2 levels was not present in younger mice, indicating a correlation between SERCA2 elevation and LTP increase in Dgcr8$^{+/-}$ mice.

To test whether this increase in SERCA2 was necessary for enhanced LTP in Dgcr8$^{+/-}$ mice, LTP was measured in the presence of the SERCA inhibitor thapsigargin (4 µM). SERCA inhibition rescued the LTP increase in Dgcr8$^{+/-}$ slices to wild-type levels. In the absence of thapsigargin, the fEPSP slope increased measured six hours after induction was approximately 120% stronger than in the presence of thapsigargin in slices from Dgcr8$^{+/-}$ mice (8 mice: 21 slices vehicle, 21 slices thapsigargin; p=0.014). Furthermore, in the presence of thapsigargin, LTP in Dgcr8$^{+/-}$ mice did not significantly differ from that in wild-type animals, indicating full rescue (p=0.854). As previously shown (Earls, et al. (2010) supra), thapsigargin did not affect LTP measured in slices from wild-type littermates (8 mice: 24 slices vehicle, 19 slices thapsigargin; p=0.974). These results indicate that SERCA2 is necessary for the observed LTP increase in mature Dgcr8$^{+/-}$ hippocampus.

Example 4

Identification of MicroRNAs Responsible for Enhanced LTP in Mouse Models of 22q11DS Dgcr8 is a miRNA biogenesis gene, and miRNAs typically act as negative regulators of protein translation. DGCR8 binds to primary miRNA transcript hairpins and recruits the nuclease DROSHA, which cleaves the hairpins. Further processing produces mature miRNAs that bind to complementary seed sites in the 3'-untranslated regions (3'-UTRs) of target mRNA transcripts and negatively regulate protein translation through recruitment of the RNA-induced silencing complex (Bartel (2009) Cell 136:215). It was therefore determined whether SERCA2 is upregulated in 22q11DS brains due to the progressive loss of specific miRNAs. To identify potentially responsible miRNAs, a microarray comparison of hippocampal miRNAs was performed between Df(16)1/+ and wild-type littermates (7 mice per genotype) at 16 weeks, the age of onset of the LTP and SERCA2 increase. No miRNAs were elevated, but fifty miRNAs were significantly reduced in the Df(16)1/+ mutants (Table 1). Using qPCR, the depletion of mature forms of 20 of these miRNAs was verified in the Df(16)1/+ hippocampus. For a subset of these miRNAs, their depletion was also verified in the Dgcr8$^{+/-}$ hippocampus at 16 weeks.

TABLE 1

| microRNA ID | Rank | p Value | Fold Change |
|---|---|---|---|
| miR-185 | 1 | 6.14E−12 | −3.29 |
| miR-229* | 2 | 8.57E−09 | −1.88 |
| miR-337-3p | 3 | 2.07E−07 | −1.88 |
| miR-411 | 4 | 2.1E−06 | −1.75 |
| miR-411* | 5 | 1.49E−06 | −1.75 |
| miR-874 | 6 | 1.12E−05 | −1.71 |
| miR-374 | 7 | 1.5E−05 | −1.71 |
| miR-379 | 8 | 7.36E−06 | −1.68 |
| miR-337-5p | 9 | 5E−07 | −1.67 |
| miR-329 | 10 | 1.64E−05 | −1.65 |
| miR-674* | 11 | 2.18E−06 | −1.63 |
| miR-323-3p | 12 | 2.17E−07 | −1.60 |
| miR-582-5p | 13 | 3.21E−06 | −1.57 |
| miR-98 | 14 | 1.43E−07 | −1.54 |
| miR-672 | 15 | 2.29E−08 | −1.54 |
| miR-25 | 16 | 1.13E−05 | −1.54 |
| miR-421 | 17 | 3.44E−07 | −1.53 |
| miR-409-5p | 18 | 5.31E−06 | −1.53 |
| miR-872 | 19 | 2.25E−05 | −1.52 |
| miR-532-3p | 20 | 2.41E−07 | −1.52 |
| miR-425 | 21 | 5.7E−06 | −1.52 |
| miR-341 | 22 | 2.14E−05 | −1.52 |
| miR-532-5p | 23 | 2.33E−05 | −1.51 |
| miR-378 | 24 | 3.87E−06 | −1.51 |
| miR-192 | 25 | 5.54E−05 | −1.51 |
| miR-380-3p | 26 | 1.97E−05 | −1.50 |
| miR-541 | 27 | 1.13E−06 | −1.49 |
| miR-873 | 28 | 3.71E−06 | −1.49 |
| miR-186 | 29 | 2.37E−05 | −1.49 |
| miR-378* | 30 | 1.11E−05 | −1.48 |
| miR-361 | 31 | 3.65E−06 | −1.48 |
| miR-467b | 32 | 2.52E−06 | −1.47 |

TABLE 1-continued

| microRNA ID | Rank | p Value | Fold Change |
|---|---|---|---|
| miR-151-5p | 33 | 1.58E-06 | -1.47 |
| miR-28 | 34 | 1.71E-05 | -1.46 |
| miR-22* | 35 | 5.09E-05 | -1.46 |
| miR-409-3p | 36 | 1.63E-06 | -1.44 |
| miR-340-3p | 37 | 2.33E-05 | -1.44 |
| miR-350 | 38 | 2.98E-05 | -1.43 |
| miR-331-3p | 39 | 1.17E-06 | -1.43 |
| miR-423-5p | 40 | 3.47E-06 | -1.42 |
| miR-382 | 41 | 3.6E-07 | -1.42 |
| miR-139-5p | 42 | 1.84E-06 | -1.41 |
| miR-377 | 43 | 7.78E-05 | -1.41 |
| miR-342-3p | 44 | 1.62E-06 | -1.41 |
| miR-15b | 45 | 2.31E-05 | -1.37 |
| miR-338-3p | 46 | 4.29E-05 | -1.36 |
| miR-335-3p | 47 | 1.58E-05 | -1.35 |
| miR-485 | 48 | 6.64E-05 | -1.32 |
| miR-23b | 49 | 5.84E-06 | -1.29 |
| miR-676 | 50 | 1.23E-05 | -1.28 |

MiRNAs affect their target mRNAs by binding to complementary seed sites within the 3'-UTR and recruiting the RNA-induced silencing complex to the transcript to prevent translation (Ambros (2004) *Nature* 341:350). Using the miR-target-prediction algorithms miRBase (Enright, et al. (2003) *Genome Biol.* 5:R1), TargetScan (Lewis, et al. (2005) *Cell* 120:15), DIANA-microT v3.0 (Kiriakidou, et al. (2004) *Genes Dev.* 18:1165), and miRDB (Wang & El Naga (2008) *Bioinformatics* 24:325), potential seed sites for miRNAs within the 3'UTR of the murine Serca2 transcript were identified (Table 2). Of the miRNAs depleted in the 22q11DS mice, three were predicted to target the SERCA2 3'UTR: miR-25, -98, and -185. Depletion of mature forms of miR-25 and miR-185 in Df(16)1/+ mice was also verified using qPCR. However, depletion of mature miR-98 in Df(16)1/+ mice could not be determined due to the AT-rich nature of this miRNA. However, it was posited that the depletion of any of these miRNAs contributes to SERCA2 upregulation and abnormal LTP in 22q11DS mouse models.

TABLE 2

| miRBase | | TargetScan | | miRDB | | microT v3.0 | |
|---|---|---|---|---|---|---|---|
| miRNA | Score | miRNA | Score | miRNA | Score | miRNA | Score |
| 369.3p | 298 | 363 | -0.39 | 4661 | 99 | 92 | 27.53 |
| 1190 | 285 | 32 | -0.38 | 544 | 90 | 30a-5p | 27.21 |
| 25* | 164 | 92b | -0.38 | 654-3p | 86 | 30e | 27.1 |
| 466g | 162 | 367 | -0.38 | 805 | 83 | 30d | 27.06 |
| 544 | 162 | 25* | -0.38 | 764-3p | 82 | 30c | 26.94 |
| 363 | 159 | 92a | -0.38 | 367 | 78 | 30b | 26.93 |
| 450a-3p | 159 | 544 | -0.42 | 25* | 76 | Let-7b | 23.67 |
| 764-3p | 157 | 298 | -0.31 | 151-3p | 75 | Let-7c | 23.48 |
| 142-3p | 155 | 804 | -0.13 | 363 | 73 | Let-7g | 23.34 |
| 574-3p | 155 | 509-3p | -0.17 | 92a | 73 | 98* | 23.29 |
| 1198 | 146 | 470 | -0.37 | 92b | 72 | Let-7i | 23.29 |
| 139-5p | 152 | 450b-5p | -0.38 | 32 | 71 | Let-7f | 23.29 |
| 135a | 151 | 668 | -0.13 | 679 | 67 | Let-7a | 23.28 |
| 135b | 151 | 4661 | -0.40 | 568 | 66 | 32 | 22.8 |
| 452 | 151 | 764-3p | -0.40 | 181b | 63 | Let-7e | 17.44 |
| 654-3p | 150 | 369-3p | -0.22 | 181d | 61 | 148b | 14.78 |
| 367 | 149 | 466g | -0.43 | 496 | 61 | 152 | 14.6 |
| 4661 | 149 | 654-3p | -0.24 | 181c | 60 | 148a | 13.56 |
| 33 | 148 | 1198 | -0.11 | 181a | 60 | 363 | 13.43 |
| 466f-3p | 148 | 450a-3p | -0.18 | 509-5p | 60 | 200a | 12.71 |
| 539 | 148 | 126-5p | -0.18 | 466g | 59 | 141 | 12.71 |
| 707 | 148 | 135 | -0.16 | 142-3p | 58 | 181d | 11.77 |
| 92b | 148 | 425 | -0.08 | 376a | 58 | 181b | 11.72 |
| 128 | 147 | 489 | -0.07 | 338-5p | 54 | 381 | 10.45 |
| 376a | 147 | 142-3p | -0.44 | 466f-3p | 53 | 301 | 9.67 |
| 323-3p | 146 | 763 | -0.20 | 1944 | 51 | 721 | 9.58 |
| 345-3p | 146 | 345-3p | -0.16 | | | 182 | 9.58 |
| 501-3p | 146 | 19b | -0.12 | | | 301b | 9.56 |
| 669d | 146 | 19a | -0.12 | | | 712 | 9.46 |
| 181a | 145 | 376a | -0.23 | | | 130b | 9.41 |
| 298 | 145 | 762 | -0.19 | | | 130a | 9.38 |
| 804 | 145 | 128 | -0.21 | | | 200c | 8.91 |
| 380-5p | 144 | 882 | -0.09 | | | 200b | 8.91 |
| 876-3p | 144 | 185* | -0.09 | | | 367 | 8.9 |
| 879 | 144 | 539 | -0.20 | | | 25* | 8.17 |
| 195 | 143 | 340-5p | -0.17 | | | 707 | 8.05 |
| 291b-3p | 143 | 338-5p | -0.17 | | | 429 | 7.8 |
| 669k | 143 | 770-5p | -0.19 | | | | |
| 92a | 143 | 139-5p | -0.18 | | | | |
| 126-5p | 142 | 487b | -0.10 | | | | |
| 301a | 142 | 707 | -0.13 | | | | |
| 500 | 142 | 377 | -0.12 | | | | |
| 669h-3p | 142 | 326 | -0.10 | | | | |
| 181b | 141 | 330 | -0.10 | | | | |
| 763 | 141 | 761 | -0.15 | | | | |
| 105 | 140 | 214 | -0.15 | | | | |
| 154 | 140 | 379 | -0.05 | | | | |
| 32 | 140 | 466f-3p | -0.24 | | | | |
| 377 | 140 | 720 | -0.06 | | | | |
| 450b-5p | 140 | 139 | -0.11 | | | | |
| 470 | 140 | 582-5p | -0.10 | | | | |
| 762 | 140 | | | | | | |

Example 5

Rescue of the LTP Increase in Dgcr8$^{+/-}$ Mice by Presynaptic Restoration of miR-25 or miR-185

To test whether depletion of miR-25 and miR-185 is required for the observed LTP increase in 22q11DS models, miR-25 or miR-185 were restored in hippocampal neurons of Dgcr8$^{+/-}$ mice to rescue the LTP phenotype. To do this, recombinant adeno-associated viruses (AAV) were generated that encode GFP and either miR-25 or miR-185 under control of the neuron-specific Synapsin promoter to infect adult neurons in vivo. Because the increase in LTP measured at CA3-CA1 synapses in mature Df(16)1/+ hippocampus is caused by presynaptic abnormalities (Earls, et al. (2010) supra), virus was injected into the CA3 region of the hippocampus in vivo. Injections were performed at 10 weeks of age, before the onset of LTP abnormalities. AAV expressing a given miRNA as injected into one hemisphere and an empty AAV (expressing only GFP) into the contralateral hemisphere as a control. LTP was then measured in both miR-injected and control-injected hippocampi at 16 weeks. AAV-driven GFP expression was robust in presynaptic CA3 neurons, but GFP was absent from postsynaptic CA1 neurons. Using qPCR, it was determined that the levels of miR-25 or miR-185 were elevated following injection of AAV-miR-25 or AAV-miR-185, respectively, but not following injection of the control AAV. Because miRNA levels were measured throughout the hippocampus, whereas the rescue viruses were only injected in the CA3 region, the levels of miRs measured in these experiments were an underestimate.

Further, to verify that miR-25 and miR-185 target the Serca2 transcript and thus affect SERCA2 protein levels, these viruses were injected into the CA3 region of four wild-type animals at 10 weeks of age. GFP-only vector was injected on the contralateral side as a control. At 16 weeks of age, hippocampi were harvested and quantitative western blot analysis was used to compare SERCA2 levels. This analysis indicated that SERCA2 decreased with overexpression of either miR-25 or miR-185. As with the qPCR results, this is an underestimation of the effect of these miRNAs on SERCA2, because the injection was specific to CA3, while western blot analysis was performed for the entire hippocampus.

Presynaptic expression of either miR-25 or miR-185 was sufficient to rescue the increased LTP in the Dgcr8$^{+/-}$ hippocampus. These results indicate that presynaptic depletion of SERCA2-targeting miRNAs causes the LTP increase in 22q11 mouse models, and restoration of any of these miRNAs is sufficient to rescue this abnormality in synaptic plasticity.

Example 6

Elevation of SERCA2 in Postmortem Brain Tissue from Patients with Schizophrenia

It was previously shown that SERCA2 is elevated in the hippocampus of the Df(16)1/+ mouse model of 22q11DS (Earls, et al. (2010) supra). However, the hippocampus is clearly not the only brain region involved in psychiatric disease associated with the deletion. To determine the specificity of this upregulation, SERCA2 levels were tested in various Df(16)1/+ tissues. SERCA2 was elevated in various brain regions of Df(16)1/+ mice, including the cortex (125.2%±5.6% of the wild-type level, p=0.012; 4 mice per genotype) and cerebellum (124.6%±7.5% of the wild-type level, p=0.048; 4 mice per genotype), but not in non-neural tissues such as liver (96.9%±4.7% of the wild-type level, p=0.689; 3-4 mice per genotype). These findings indicate that changes in SERCA2 expression are brain-specific and found throughout the brain.

Because the elevation of SERCA2 has serious consequences on neural function, it was determined whether the molecular findings in the 22q11DS mouse models would translate to human disease. Therefore, SERCA2 levels were compared in postmortem tissue samples from the hippocampus and prefrontal cortex of patients with schizophrenia and unaffected controls. This comparison revealed a significant increase in SERCA2 levels in both brain regions of schizophrenic patients. This finding indicates that elevation in SERCA2 protein contributes to the symptoms of schizophrenia. The seed sites for hsa-miR-25, hsa-miR-98, and hsa-miR-185 are conserved in the 3'-UTR of human SERCA2B, indicating that modulation by these miRs is a potential mechanism of SERCA2 protein overexpression in schizophrenia.

What is claimed is:

1. A method for diagnosing susceptibility to developing a learning or mental disorder comprising
   (a) obtaining a biological sample from a subject;
   (b) determining the level of at least one microRNA (miR) gene product selected from the group of miR-25, miR-98 and miR-185 with a miR-25 oligonucleotides consisting of SEQ ID NO:7, SEQ ID NO:8, SEQ ID NO:9 and SEQ ID NO:35, miR-98 oligonucleotides consisting of SEQ ID NO:10, SEQ ID NO:11, SEQ ID NO:12 and SEQ ID NO:28, or a miR-185 oligonucleotides consisting of SEQ ID NO:13, SEQ ID NO:14 and SEQ ID NO:15, respectively;
   (c) comparing the level of microRNA in the biological sample to a control sample; and
   (d) diagnosing susceptibility to developing a learning or mental disorder, wherein a decrease in the level of the microRNA as compared to the control sample indicates that the subject is susceptible to developing a learning or mental disorder.

2. The method of claim 1, wherein the mental disorder is a psychiatric disease.

3. The method of claim 2, wherein the psychiatric disease or mental disorder is selected from the group consisting of schizophrenia, Alzheimer's disease, bipolar disorder, schizoaffective disorder, 22q11 deletion syndrome, attention-deficit hyperactivity disorder, obsessive-compulsive disorder and autism spectrum disorder.

4. A method for diagnosing a subject suspected of having a learning or mental disorder comprising
   (a) obtaining a biological sample from a subject;
   (b) determining the level of at least one microRNA (miR) gene product selected from the group of miR-25, miR-98 and miR-185 with a miR-25 oligonucleotides consisting of SEQ ID NO:7, SEQ ID NO:8, SEQ ID NO:9 and SEQ ID NO:35, miR-98 oligonucleotides consisting of SEQ ID NO:10, SEQ ID NO:11, SEQ ID NO:12 and SEQ ID NO:28, or miR-185 oligonucleotides consisting of SEQ ID NO:13, SEQ ID NO:14 and SEQ ID NO:15, respectively;
   (c) comparing the level of microRNA in the biological sample to a control sample; and
   (d) diagnosing a learning or mental disorder, wherein a decrease in the level of the microRNA as compared to the control sample indicates that the subject has a learning or mental disorder.

5. The method of claim 4, wherein the mental disorder is a psychiatric disease.

6. The method of claim 5, wherein the psychiatric disease or mental disorder is selected from the group consisting of schizophrenia, Alzheimer's disease, bipolar disorder, schizoaffective disorder, 22q11 deletion syndrome, attention-deficit hyperactivity disorder, obsessive-compulsive disorder and autism spectrum disorder.

* * * * *